United States Patent
Blandino et al.

(10) Patent No.: US 11,236,288 B2
(45) Date of Patent: Feb. 1, 2022

(54) FRAGRANCE MATERIALS

(71) Applicant: TAKASAGO INTERNATIONAL CORPORATION, Tokyo (JP)

(72) Inventors: Maureen Blandino, Dumont, NJ (US); Michael E. Lankin, High Bridge, NJ (US)

(73) Assignee: TAKASAGO INTERNATIONAL CORPORATION, Tokyo (JP)

( * ) Notice: Subject to any disclaimer, the term of this patent is extended or adjusted under 35 U.S.C. 154(b) by 0 days.

(21) Appl. No.: 15/734,683

(22) PCT Filed: Jun. 4, 2019

(86) PCT No.: PCT/US2019/035367
§ 371 (c)(1),
(2) Date: Dec. 3, 2020

(87) PCT Pub. No.: WO2019/236562
PCT Pub. Date: Dec. 12, 2019

(65) Prior Publication Data
US 2021/0230504 A1 Jul. 29, 2021

Related U.S. Application Data

(60) Provisional application No. 62/680,403, filed on Jun. 4, 2018.

(51) Int. Cl.
| | | |
|---|---|---|
| *C11D 3/50* | (2006.01) |
| *C11B 9/00* | (2006.01) |
| *A61K 8/49* | (2006.01) |
| *A61Q 5/02* | (2006.01) |
| *C07D 333/08* | (2006.01) |
| *C11D 3/00* | (2006.01) |
| *C11D 3/34* | (2006.01) |

(52) U.S. Cl.
CPC .......... *C11B 9/0076* (2013.01); *A61K 8/4986* (2013.01); *A61Q 5/02* (2013.01); *C07D 333/08* (2013.01); *C11D 3/001* (2013.01); *C11D 3/3481* (2013.01)

(58) Field of Classification Search
CPC ...... A61K 8/4986; C11D 3/505; C11B 9/0076
See application file for complete search history.

(56) References Cited

U.S. PATENT DOCUMENTS

| | | | | |
|---|---|---|---|---|
| 2,512,596 A * | 6/1950 | Arnold | ................. | C07D 333/08 549/80 |
| 2,560,610 A * | 7/1951 | Wagner | ................ | C07D 333/08 549/83 |
| 2,616,897 A * | 11/1952 | Pines | ...................... | C08F 28/06 549/80 |
| 2,666,765 A * | 1/1954 | Pines | ................... | C07D 333/08 549/80 |
| 2,689,855 A * | 9/1954 | Wagner | ................ | C07D 333/08 549/80 |
| 2002/0183516 A1 * | 12/2002 | Denmark | .............. | C07F 7/0836 540/555 |

FOREIGN PATENT DOCUMENTS

JP    S 61-57511 A    3/1986

OTHER PUBLICATIONS

International Search Report dated Sep. 4, 2019 in International Application No. PCT/US2019/035367.

* cited by examiner

*Primary Examiner* — John R Hardee
(74) *Attorney, Agent, or Firm* — Baker Botts L.L.P.

(57) ABSTRACT

The synthesis and application of a compound having unique and desired fragrance characteristics is provided herein. The compound of the present disclosure can be employed alone or incorporated as a fragrance component in fragrance compositions. The application is also directed to consumer products comprising such compound and/or fragrance compositions.

12 Claims, No Drawings

FRAGRANCE MATERIALS

CROSS-REFERENCE TO RELATED APPLICATIONS

This application is a U.S. National Stage Patent Application under 35 U.S.C. § 371 of International Patent Application No. PCT/US2019/035367, filed on Jun. 4, 2019, which claims priority to U.S. Provisional Patent Application Ser. No. 62/680,403, filed on Jun. 4, 2018, the contents of each of which are hereby incorporated by reference in their entireties.

FIELD

The present application relates to a compound useful as a fragrance component in fragrance compositions.

BACKGROUND

There is a continuing interest in the preparation of synthetic fragrance components to provide pleasing organoleptic characteristics in new fragrances. For a wide variety of consumer products, the decision to purchase the product or not can be based on whether the scent of the product is perceived as pleasing to the consumers. This is particularly true for consumer products such as fine fragrance products, candles, and the like wherein the scent is the main reason for the purchase, or consumer products such as laundry detergents wherein the scent is intended to remain on the consumer's clothing.

Thus, there remains a need and demand for unique fragrance compounds. There is also a need for fragrance compositions with pleasing and consumer preferred odor profiles for use in multiple consumer products.

SUMMARY

The present disclosure is directed to the synthesis and application of a compound having unique and desired fragrance characteristics. The compound of the present disclosure can be employed alone or incorporated into fragrance compositions.

In certain embodiments, the presently disclosed subject matter provides the compound represented by Formula I:

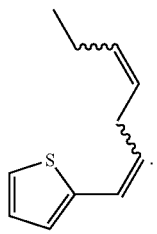

The presently disclosed subject matter also provides for fragrance composition comprising the compound of Formula I.

In certain embodiments of the present disclosure, the fragrance composition can comprise about a 50/50 mixture of cis-cis isomers and cis-trans isomers of the compound of Formula I.

In particular embodiments, the present disclosure provides for a fragrance composition, wherein the composition can comprise about a 50/50 mixture of 2-((1Z,4Z)-hepta-1,4-dien-1-yl)thiophene and 2-((1E,4Z)-hepta-1,4-dien-1-yl)thiophene. In a particular embodiment, the concentration of the compound of Formula I in the fragrance compositions disclosed herein can be from about 0.01% to about 20% by weight, based on the total weight of the fragrance composition.

In certain embodiments, the fragrance composition can further comprise one or more compounds selected from the group consisting of one or more aldehydic compound(s), one or more animalic compound(s), one or more balsamic compound(s), one or more citrus compound(s), one or more floral compound(s), one or more fruity compound(s), one or more gourmand compound(s), one or more green compound(s) one or more herbaceous compound(s) one or more marine compound(s), one or more mossy compound(s), one or more musk compound(s), one or more piney compound(s), one or more powdery compound(s), one or more spicy compound(s) and/or one or more woody and/or amber compound(s), and combinations thereof.

Another aspect of the present disclosure provides a consumer product comprising the compound of Formula I. In certain embodiments, the consumer product can include a fragrance composition comprising the compound of Formula I. In particular embodiments, the consumer product can include a fragrance composition comprising about a 50/50 mixture of cis-cis isomer and cis-trans isomer of the compound of Formula I.

DETAILED DESCRIPTION

As noted above, there remains a need and demand in the art for unique fragrance compositions. The presently disclosed subject matter addresses this need through the compound disclosed herein and/or new fragrance compositions comprising the disclosed compound.

For clarity, and not by way of limitation, the detailed description is divided into the following subsections:
1. Definitions;
2. Fragrance Compound;
3. Fragrance Compositions; and
4. Use of Fragrance Compositions in Consumer Products.

1. Definitions

The terms used in this specification generally have their ordinary meanings in the art, within the context of this disclosure and in the specific context where each term is used. Certain terms are discussed below, or elsewhere in the specification, to provide additional guidance to a person of ordinary skill in the art describing the compounds, compositions and methods of the disclosure and how to make and use them.

As used herein, the use of the word "a" or "an" when used in conjunction with the term "comprising" in the claims and/or the specification can mean "one," but it is also consistent with the meaning of "one or more," "at least one," a plurality, and "one or more than one." Still further, the terms "having," "including," "containing" and "comprising" are interchangeable and one of skill in the art is cognizant that these terms are open ended terms.

The term "about" or "approximately" means within an acceptable error range for the particular value as determined by one of ordinary skill in the art, which will depend in part on how the value is measured or determined, i.e., the limitations of the measurement system. For example, "about" can mean within 3 or more than 3 standard deviations, per the practice in the art. Alternatively, "about" can mean a range of up to 20%, preferably up to 10%, more preferably up to 5%, and more preferably still up to 1% of a given value. Alternatively, particularly with respect to biological systems or processes, the term can mean within an order of magnitude, preferably within 5-fold, and more preferably within 2-fold, of a value.

As used herein, the term "isomers" refers to different compounds that have the same molecular formula but differ in arrangement and configuration of the atoms. Also, as used herein, the term "stereoisomer" refers to any of the various stereo isomeric configurations which can exist for a given compound of the presently disclosed subject matter and includes geometric isomers. It is understood the compound of the present disclosure contains double bonds, where the substituents can be E or Z configuration. Also, as used herein, the terms "constitutional isomers" refers to different compounds which have the same numbers of, and types of, atoms but the atoms are connected differently.

As used herein, the term "fragrance composition" refers to a mixture comprising one or more fragrance compounds, in any of their forms, and one or more solvents or perfuming co-ingredients. As known in the art, a fragrance composition contains one or more fragrance compounds in order to impart an olfactory note to the consumer product formulation (e.g., a household cleaner, perfume, or other consumer product) to which it is added. In one embodiment, the fragrance composition contains two or more fragrance compounds which, collectively and in combination with the solvent to which they are added, impart an intended olfactory note (e.g., a hedonically pleasing "tropical" note) to a human in close proximity to the fragrance composition. In general terms, perfuming co-ingredients belong to chemical classes as varied as alcohols, aldehydes, ketones, esters, ethers, acetates, nitriles, terpene hydrocarbons, nitrogenous or sulphurous heterocyclic compounds and essential oils of natural or synthetic origin, and are known to perfumers of ordinary skill in the art. Many of these ingredients are listed in reference texts such as S. Arctander, *Perfume and Flavor Chemicals,* 1969, Montclair, N.J., USA or any of its more recent versions, each of which are hereby incorporated by reference in their entireties.

As used herein, the term "accord" refers to a fragrance composition that contains a mixture of two or more different fragrance compounds that creates a specific smell, odor or scent. One or more "accords" can be utilized as part of fragrance composition.

As used herein, the term "consumer product" or "end product" refers to composition that is in a form ready for use by the consumer for the marketed indication. A solvent suitable for use in a consumer product is a solvent that, when combined with other components of the end product, will not render the consumer product unfit for its intended consumer use.

2. Fragrance Compound

The present disclosure is directed to the synthesis and application of a fragrance compound having unique and desired fragrance characteristics.

In certain embodiments, the presently disclosed subject matter provides a compound of Formula I,

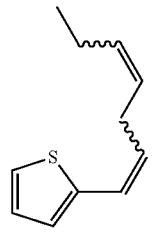

In certain embodiments, the compound of the presently disclosed subject matter can include stereoisomers and constitutional isomers of said compound listed herein. For example, in certain embodiments, the compound can include stereoisomers including cis-cis isomer and trans-cis isomer of the compound of Formula I. The cis-cis isomer is 2-((1Z,4Z)-hepta-1,4-dien-1-yl)thiophene. The trans-cis isomer is 2-((1E,4Z)-hepta-1,4-dien-1-yl)thiophene. In one embodiment, the presently disclosed compound can be about a 50/50 mixture of cis-cis isomer and trans-cis isomer of said compound listed herein. For example, in particular embodiments, the presently disclosed compound can be about a 50/50 mixture of 2-((1Z,4Z)-hepta-1,4-dien-1-yl)thiophene and 2-((1E,4Z)-hepta-1,4-dien-1-yl)thiophene. In another embodiment, the compound of the presently disclosed subject matter can include a greater amount of cis-cis isomer than trans-cis isomer of said compound listed herein. For example, in certain embodiments, the presently disclosed compound can be about an 80/20 mixture to less than about a 95/5 mixture of cis-cis isomer and trans-cis isomer. In particular embodiments, the presently disclosed compound can be about an 80/20 mixture, about a 90/10 mixture, or about a 95/5 mixture of cis-cis isomer and trans-cis isomer. Alternatively, in another embodiment, the compound of the presently disclosed subject matter can include a greater amount of trans-cis isomer than cis-cis isomer of said compound listed herein. For example, in certain embodiments, the presently disclosed compound can be from about an 80/20 mixture to less than about a 95/5 mixture of trans-cis isomer and cis-cis isomer. In particular embodiments, the presently disclosed compound can be an 80/20 mixture, a 90/10 mixture, or a 95/5 mixture of trans-cis isomer and cis-cis isomer.

The compound of the presently disclosed subject matter can include cis-trans and trans-trans stereoisomers of said compound listed herein. For example, in certain embodiments, trace amounts of cis-trans and trans-trans isomers can be included in the mixture. The cis-trans isomer is 2-((1Z,4E)-hepta-1,4-dien-1-yl)thiophene. The trans-trans isomer is 2-((1E,4E)-hepta-1,4-dien-1-yl)thiophene. In certain embodiments, the compound of the presently disclosed subject matter can include conjugated constitutional isomers of said compound listed herein. For example, in certain embodiments, trace amounts of conjugated constitutional isomers can be included in the mixture. The conjugated constitutional isomers can include, for example, 2-((1Z,3E)-hepta-1,3-dien-1-yl)thiophene, 2-((1E,3E)-hepta-1,3-dien-1-yl)thiophene, and combinations thereof. The presently disclosed compound is synthetic. Synthetic versions of the compound can include those obtained via chemical synthesis or isolated through chemical processes, whether artificial or nature-identical.

In one embodiment, the presently disclosed compound can be prepared synthetically, for example, through a Wittig reaction between a cis-3-hexenyl-triphenylphosphonium halide salt and thiophene carboxaldehyde. A person skilled in the art will appreciate that a wide variety of synthetic methods can be used to prepare the presently disclosed compound.

The compound of the disclosed subject matter provides unique and unexpected odor properties. More particularly, the compound of Formula I provides strong green floral notes, including without limitation violet leaf, tomato, and geranium notes.

3. Fragrance Compositions

In certain embodiments, the above described compound can be provided in a fragrance composition. Certain embodiments of the presently disclosed subject matter provide a method to modify, enhance or improve the odor properties of a fragrance composition by adding to the composition an effective quantity of the compound of Formula I. In one embodiment, about a 50/50 mixture of cis-cis isomers and trans-cis isomers of the compound of Formula I can be used in a fragrance composition. In particular embodiments, the fragrance composition can include about a 50/50 mixture of 2-((1Z,4Z)-hepta-1,4-dien-1-yl)thiophene and 2-((1E,4Z)-hepta-1,4-dien-1-yl)thiophene.

In certain embodiments, the present disclosure provides a fragrance composition comprising a mixture of isomers of the compound of Formula I, wherein the ratio of cis-cis isomers to trans-cis isomers can be from about 70:30 to less than about 100:0. In certain embodiments, the ratio of cis-cis isomers to trans-cis isomers in the fragrance composition can be from about 80:20 to less than about 100:0. In certain other embodiments, the ratio of cis-cis isomers to trans-cis isomers in the fragrance composition can be from about 90:10 to less than about 100:0. In certain other embodiments, the ratio of cis-cis isomers to trans-cis isomers in the fragrance composition can be from about 99:1 to less than about 100:0. In particular embodiments, the ratio of cis-cis isomers to trans-cis isomers in the fragrance composition can be about 70:30, about 80:20, about 90:10, about 95:5, or about 99:1.

In other embodiments, the present disclosure provides a fragrance composition comprising a mixture of isomers of the compound of Formula I, wherein the ratio of trans-cis isomers to cis-cis isomers can be from about 70:30 to less than about 100:0. In certain embodiments, the ratio of trans-cis isomers to cis-cis isomers in the fragrance composition can be from about 80:20 to less than about 100:0. In certain other embodiments, the ratio of trans-cis isomers to cis-cis isomers in the fragrance composition can be from about 90:10 to less than about 100:0. In certain other embodiments, the ratio of trans-cis isomers to cis-cis isomers in the fragrance composition can be from about 99:1 to less than about 100:0. In particular embodiments, the ratio of trans-cis isomers to cis-cis isomers in the fragrance composition can be about 70:30, about 80:20, about 90:10, about 95:5, or about 99:1.

The fragrance composition can additionally include one or more isomers of the presently disclosed compound of Formula I selected from the group consisting of cis-trans (2-((1Z,4E)-hepta-1,4-dien-1-yl)thiophene); trans-trans (2-((1E,4E)-hepta-1,4-dien-1-yl)thiophene); and conjugated constitutional isomers (i.e., 2-((1Z,3E)-hepta-1,3-dien-1-yl)thiophene and 2-((1E,3E)-hepta-1,3-dien-1-yl)thiophene). In particular embodiments, one or more isomers additionally included in the fragrance composition can be present in the fragrance composition in trace amounts.

The compound of Formula I is particularly valuable as being capable of imparting green, floral notes to a fragrance composition, including without limitation green, violet leaf, and geranium notes.

For fragrance applications, the concentration of the compound of Formula I is based on the total weight of the composition into which the fragrance compound is incorporated. For fragrance compositions, typical concentrations of the presently disclosed compounds can range from about 0.01% to about 20% by weight, from about 0.01% to about 10% by weight, from about 0.01% to about 5% by weight, from about 0.1% to about 10% by weight, or from about 1% to about 5% by weight, based on the total weight of the fragrance composition into which the presently disclosed compound is incorporated. In particular embodiments, the presently disclosed compounds can be present in the fragrance composition in an amount of about 0.01%, about 0.1%, about 0.5%, about 0.8%, about 1%, about 3%, or about 5% by weight, based on the total weight of the fragrance composition. In further embodiments, the presently disclosed compounds can be present in the fragrance composition in an amount of at least about 0.01%, at least about 0.1%, at least about 0.5%, at least about 1%, or at least about 5% by weight, based on the total weight of the fragrance composition. Those skilled in the art are able to employ the desired level of the presently disclosed compound to provide the desired fragrance and intensity.

The compound of the presently disclosed subject matter can be combined with one or more fragrance compounds from various fragrance categories to form accords or fragrance compositions, such fragrance categories including but not limited to one or more aldehydic compound(s), one or more animalic compound(s), one or more balsamic compound(s), one or more citrus compound(s), one or more floral compound(s), one or more fruity compound(s), one or more gourmand compound(s), one or more green compound(s) one or more herbaceous compound(s) one or more marine compound(s), one or more mossy compound(s), one or more musk compound(s), one or more piney compound(s), one or more powdery compound(s), one or more spicy compound(s) and/or one or more woody and/or amber compound(s), and combinations thereof.

In certain embodiments, the fragrance composition can include the compound of the presently disclosed subject matter and one or more fragrance compounds including one or more animalic compound(s), one or more floral compound(s), one or more fruity compound(s), one or more gourmand compound(s), one or more green compound(s), and one or more herbaceous compound(s). The compound of the presently disclosed subject matter can be present in an amount of from about 1% to about 25%, from about 5% to about 15%, or about 10% by weight, based on the total weight of the fragrance composition. In particular embodiments, the presently disclosed compound can be about a 50/50 mixture of cis-cis isomers and trans-cis isomers of the compound of Formula I. The one or more animalic compound(s) can be present in an amount of from about 0.0001% to about 5%, from about 0.001% to about 5%, or from about 0.01% to about 1% by weight, based on the total weight of the fragrance composition. The one or more floral compound(s) can be present in an amount of from about 1% to about 50%, from about 5% to about 45%, or from about 15% to about 40% by weight, based on the total weight of the fragrance composition. The one or more fruity compound(s) can be present in an amount of from about 1% to about 40%, from about 1% to about 30%, or from about 25% to about 30% by weight, based on the total weight of the fragrance composition. The one or more gourmand compound(s) can be present in an amount of from about 1% to about 20%, from about 1% to about 15%, or from about 1% to about 10% by weight, based on the total weight of the fragrance composition. The one or more green compound(s) can be present in an amount of from about 0.01% to about 5%, from about 0.2% to about 2%, or from about 0.5% to about 1.5% by weight, based on the total weight of the fragrance composition. The one or more herbaceous compound(s) can be present in an amount of from about 0.001% to about 5%, from about 0.001% to about 2%, or from about 0.01% to about 1.5% by weight, based on the total weight of the fragrance composition. The fragrance composition can further include one or more solvents. The one or more solvents can be present in an amount of from about 1% to about 25%, from about 5% to about 20%, or about 15% by weight, based on the total weight of the fragrance composition. In certain embodiments, the one or more solvents can include dipropyleneglycol (DPG).

In certain embodiments, the fragrance composition can include the compound of the presently disclosed subject matter and one or more fragrance compounds including one or more aldehydic compound(s), one or more animalic compound(s), one or more citrus compound(s), one or more floral compound(s), one or more fruity compound(s), one or more gourmand compound(s), one or more green compound(s), one or more musk compound(s), and one or more woody and/or amber compound(s). The compound of the presently disclosed subject matter can be present in an amount of from about 0.01% to about 5%, from about 0.1% to about 2%, or about 1% by weight, based on the total weight of the fragrance composition. In particular embodiments, the presently disclosed compound can be about a 50/50 mixture of cis-cis isomers and trans-cis isomers of the compound of Formula I. The one or more aldehydic compound(s) can be present in an amount of from about 0.001% to about 10%, from about 0.01% to about 5%, or from about 0.5% to about 2% by weight, based on the total weight of the fragrance composition. The one or more animalic compound(s) can be present in an amount of from about 0.0001% to about 5%, from about 0.001% to about 5%, or from about 0.01% to about 1% by weight, based on the total weight of the fragrance composition. The one or more citrus compound(s) can be present in an amount of from about 1% to about 15%, from about 1% to about 10%, or from about 1% to about 5% by weight, based on the total weight of the fragrance composition. The one or more floral compound(s) can be present in an amount of from about 1% to about 50%, from about 5% to about 45%, or from about 15% to about 40% by weight, based on the total weight of the fragrance composition. The one or more fruity compound(s) can be present in an amount of from about 1% to about 40%, from about 1% to about 30%, or from about 25% to about 30% by weight, based on the total weight of the fragrance composition. The one or more gourmand compound(s) can be present in an amount of from about 1% to about 20%, from about 1% to about 15%, or from about 1% to about 10% by weight, based on the total weight of the fragrance composition. The one or more green compound(s) can be present in an amount of from about 0.01% to about 5%, from about 0.2% to about 2%, or from about 0.5% to about 1.5% by weight, based on the total weight of the fragrance composition. The one or more musk compound(s) can be present in an amount of from about 0.1% to about 10%, from about 0.1% to about 5%, or about 1% to about 5% by weight, based on the total weight of the fragrance composition. The one or more woody and/or amber compound(s) can be present in an amount of from about 0.01% to about 80%, from about 0.1% to about 50%, or from about 1% to about 15% by weight, or from about 1% to about 10%, or from about 2% to about 8%, or from about 3% to about 6% by weight, based on the total weight of the fragrance composition.

Non-limiting examples of suitable aldehydic compounds include acetaldehyde C-8, acetaldehyde C-9, acetaldehyde C-10, adoxal, aldehyde C-8, aldehyde C-9, aldehyde C-10, aldehyde C-11, aldehyde C-12, aldehyde C-12 lauric, aldehyde C-12 MNA, aldehyde supra, cyclomyral trans-2-decenal, trans-4-decenal cis-4-decenal, 9-decenal, myrac aldehyde, precyclemone B, trans-2-decenal, undecylenic aldehyde, 1-methyl-4-(4-methylpentyl)cyclohex-3-ene-1-carbaldehyde (VERNALDEHYDE®), and combinations thereof.

Non-limiting examples of suitable animalic compounds include 5-cyclohexadecen-1-one (AMBRETONE®), 17-oxacycloheptadec-6-en-1-one (ambrettolide), 2,5,5-trimethyl-1,3,4,4a,6,7-hexahydronaphthalen-2-ol (ambrinol), 2-Methyl-5-(5,5,6-trimethylbicyclo[2.2.1]hept-2-yl)cyclohexanone (ALDRON®), civet, p-cresol, cresyl methyl ether, indole, skatole, and combinations thereof.

Non-limiting examples of suitable balsamic compounds include benzy salicylate, cylohexyl salicylate, isopropoxy ethyl salicylate, phenethyl salicylate, styrax oil, and combinations thereof.

Non-limiting examples of suitable citrus compounds include delta-3-carene, citral, citronellal, L-citronellol, decanal, DH-L-citronellal, DH-myrcenol, limonene, myrcenol, nootkatone, sinensal, bergamot oil, grapefruit oil, lemon oil, lime oil, orange oil, tridecene-2-nitrile, yuzu core base, and combinations thereof.

Non-limiting examples of floral compounds include dimethyl octanol, tetrahydro geraniol, isobutyl salicylate, acetanisole, alpha amyl cinnamaldehyde, anisyl acetate, anisic aldehyde, benzyl acetate, bourgeonal, butyl acetate, hexyl cinnammic aldehyde, 1-citrol, cyclamen aldehyde, cyclohexyl lactone, delta-damascone, 9-decen-1-ol, dimethyl benzyl carbinol, farnesal, 1-dihydrofarnesal, ethyl linalool, 1-farnesal, farnesol, 1-dihydrofarnesol, 3-(3-Isopropylphenyl)butanal (FLORHYDRAL®), 3-(4-ethylphenyl)-2,2-dimethylpropanal (floralozone), 4-methyl-2-(2-methylpropyl)oxan-4-ol (FLOROL®), geraniol, gernayl acetate, piperonal, methyl 3-oxo-2-pentylcyclopentaneacetate (Hedione®), 2-Methyl-3-(3,4-methylenedioxyphenyl)propanal (Heliobouquet), 1-(5,6,7,8-tetrahydronaphthalen-2-yl)ethanone (FLORANTONE®), 3-(4-Isobutyl-phenyl)-2-methyl-propionaldehyde (SUZARAL®), hexyl cinnamaldehyde, hexyl salicylate, indole, alpha-ionone, beta-ionone, isopropoxy ethyl salicylate, methyl-2-((1S*,2R*)-3-oxo-2-pentylcyclopentyl)acetate (JASMODIONE®), cis-jasmone, 4-(4-hydroxy-4-methylpentyl)cyclohex-3-ene-1-carbaldehyde (KOVANOL®), laurinal, lilial, linalool, linalyl acetate, 2,4,6,-trimethyl-4-phenyl-1,3-dioxane (LOREXAN®), 2,4-Dimethyl-4,4a,5,9b-tetrahydroindeno[1,2-d][1,3]dioxine (Magnolan), (4-propan-2-ylcyclohexyl)methanol (Mayol), methyl dihydroj asomante, gamma-methyl ionone, methyl benzoate, 1-(4-Isopropylcyclohexyl) ethanol (Mugetanol), nerol, 1-(3-Methyl-benzofuran-2-yl)-ethanone (Nerolione), neryl acetate, orantha, L., 2-pentyl cyclopentanone, 2-cyclohexyl-2-cyclohexylideneacetonitrile (PEONILE®), phenoxanol, phenoxy ethyl isobutyrate, phenylacetaldehyde, phenyl ethyl alcohol, prenyl salicylate, rose oxide, rosephenone, rosyrane, terpineol, undecavertol, 2,2,5-trimethyl-5-pentylcyclopentan-1-one (VELOUTONE®), yara yara, geranium oil, rose oil, lavender oil, ylang oil, and combinations thereof.

Non-limiting examples of fruity compounds include aldehyde C-16, allyl caproate, allyl cyclohexyl proprionate, allyl heptanoate, amyl acetate, benzaldehyde, CASSIS®, L-citronellyl acetate, L-citronellyl nitrile, 3a,4,5,6,7,7a-hexahydro-4,7-methano-1h-inden-5(or 6)-yl acetate (CYCLACET®), 3a,4,5,6,7,7a-hexahydro-1H-4,7-methanoinden-1-yl propanoate (CYCLAPROP®), damascenone, beta-decalactone, gamma-decalactone, diethyl malonate, dimethyl benzyl carbinol acetate, dimethyl benzyl carbinyl butyrate, dimethyl phenyl ethyl carbinol, dimethyl sulfide, γ-dodecalactone, ethyl acetate, ethyl butyrate, ethyl caproate, ethyl decadienotate, ethyl heptoate, ethyl-2-methylbutyrate, ethyl acetoacetate, ethyl methyl phenyl glycidate, ethyl propionate, 4-methyl-2-(2-methylpropyl)oxan-4-ol (FLOROL®), ethyl tricyclo [5.2.1.02.6] decan-2 carboxylate (FRUITATE®), hexyl acetate, hexyl isobutyrate, isoamyl acetate, 6-(pent-3-en-1-yl)tetrahydro-2H-pyran-2-one (Jasmolactone), ethyl 2-methylpentanoate (manzanate), 2,6-dimethylhept-5-enal (melonal), methyl anthranilate, methyl dioxolan, methyl heptyl ketone, gamma-nonalactone, 6-nonenol, gamma-octalactone, phenyl ethyl isobutyrate, prenyl acetate, raspberry ketone, methyl(2-((4 S)-4-methyl-2-methylenecyclohexyl)propan-2-yl)sulfane (RINGONOL®), (1R, 6S)-ethyl 2,2,6-trimethylclocloxehanecarboxylate (THESARON®), tolyl aldehyde, γ-undecalactone, 3,5,5-trimethylhexyl acetate (vanoris), (2-tert-butylcyclohexyl) acetate (verdox), nopyl acetate, and combinations thereof.

Non-limiting examples of gourmand compounds include angelica lactone-alpha, caprylic acid, coumarin, ethyl fraison, ethyl vanillin, ethyl maltol (e.g., VELTOL PLUS), filbertone, 4-hydroxy-2,5-dimethyl-3(2H)-furanone (FURANEOL®), guaiacol, maple furanone, 2-acetyl pyrazine, 2,5-dimethyl pyrazine, cyclohex-3-en-1-ylmethyl-2-hydroxypropanoate, vanillin, and combinations thereof.

Non-limiting examples of green compounds include allyl amyl glycolate, cyclogalbanate, 1-(5,5-dimethyl-1-cyclohexen-1-yl)-4-Penten-1-one (DYNASCONE®), galbanolene, galbanum, trans-2-hexenal, cis-3-hexenol, hexen-1-ol, cis-3-hexenyl acetate, cis-3-hexenyl butyrate, cis-3-hexenyl formate, cis-3-hexenyl salicyclate, liffarome, 2-methoxy-2-methylheptane, methyl octine carbonate, neofolione, 2,6-nonadienal, (2R,4S)-2-methyl-4-propyl-1,3-oxathiane (OXANE®), octahydro-5-methoxy-4,7-methano-1H-indene-2-carboxaldehyde (SCENTENAL®), N-(5-methylheptan-3-ylidene)hydroxylamine (STEMONE®), styrallyl acetate, 2,4-dimethylcyclohex-3-ene-1-carbaldehyde (TRIPLAL®), undecavertol, vionil, violet methyl carbonate (e.g., VIOLET T), violet leaf extract, and combinations thereof.

Non-limiting examples of herbaceous compounds include bamboo ketone, canthoxal, carvacrol, clary sage natural oil, cymene, p., 2,6-dimethylheptan-2-ol (DIMETOL®), menthol, methyl salicylate, thymol, natural basil oil, natural *eucalyptus* oil, eucalyptol, sweet natural fennel oil, natural cedar leaf oil, and combinations thereof.

Non-limiting examples of marine compounds include 8-methyl-1,5-benzodioxepin-3-one (Calone® 1951), 3-(4-ethylphenyl)-2,2-dimethylpropanal (floralozone), 4-tert-butylphenylacetonitrile (MARENIL®), 4-[(3E)-4,8-dimethylnona-3,7-dienyl]pyridine (MARITIMA®), myrac aldehyde, ultrazure, and combinations thereof.

Non-limiting examples of mossy compounds include hinokitiol, isobutyl quinolone, isopropyl quinolone and/or methyl 2,4-dihydroxy-3,6-dimethylbenzoate (Oakmoss® #1), and combinations thereof.

Non-limiting examples of musk compounds include 17-oxacycloheptadec-6-en-1-one (ambrettolide), 5-Cyclohexadecen-1-one (AMBRETONE®), 2,2,6-trimethyl-alpha-propylcyclohexanepropanol (Dextramber) (3 aR, 5aS,9aS, 9bR)-3a,6,6,9a-Tetramethyldodecahydronaphtho[2,1-b] furan (AMBROXAN), 2,2,6-trimethyl-alpha-propylcyclohexanepropanol (Dextramber), 16-oxacyclohexadecan-1-one (EXALTOLIDE®), 4,6,6,7,8,8-hexamethyl-1,3,4,6,7,8-hexahydro-cyclopenta[g]-isochromene (GALAXOLIDE®), ((12E)-1-oxacyclohexadec-12-en-2-one (habanolide), [2-[1-(3,3-dimethylcyclohexyl) ethoxy]-2-methylpropyl]propanoate (HELVETOLIDE®), (1'R)-3-methyl-5-(2,2,3-trimethylcyclopentan-1-yl)-2-pentanone, (5E)-3-methylcyclopentadec-5-en-1-one (MUSCENONE®), 1,4-dioxacycloheptadecane-5,17-dione (Musk T), 3-methylcyclopentadecan-1-one (L-muscone), 1-(1,1,2,6-tetramethyl-3-propan-2-yl-2,3-dihydroinden-5-yl)ethanone (TRASEOLIDE™), 1-(3,5,5,6,8,8-hexamethyl-6,7-dihydronaphthalen-2-yl)ethenone (TONALID®), and combinations thereof.

Non-limiting examples of piney compounds include 1-borneol, 1-bornyl acetate, camphene, camphor gum powder, dihydroterpineol, β-pinene, and combinations thereof.

Non-limiting examples of powdery compounds include heliotropine and/or whiskey lactone (methyl octalactone).

Non-limiting examples of spicy compounds include acetyl isoeugenol, delta-caryophellene, cinnamaldehyde, cuminaldehyde, eugenol, isoeugenol, *perilla* aldehyde, cardamom oil, clove oil, ginger extract, black pepper extract, and combinations thereof.

Non-limiting examples of woody and/or amber compounds include amber core, amber extreme, (4-tert-butylcyclohexyl) acetate (Vertenex®), ambretol, 4aR,5R,7aS,9R)-Octahydro-2,2,5,8,8,9a-hexamethyl-4H-4a,9-methanoazuleno[5,6-d]-1,3-dioxole (AMBROCENIDE®), ((3aR,5aS,9aS,9bR)-3a,6,6,9a-Tetramethyldodecahydronaphtho[2,1-b]furan (AMBROXAN), 2-ethyl-4-(2,2,3-trimethyl-3-cyclo-penten-1-yl)-2-buten-1-ol (BACDANOL®), ethoxymethoxycyclododecane (Boisambrene Forte), 1,1,2,3,3-pentamethyl-2,5,6,7-tetrahydroinden-4-one (Cashmeran®), ((2R,5 S,7R,8R)-8-methoxy-2,6,6,8-tetramethyltricyclo[5.3.1.01,5]undecane (Cedramber®), cedanol, cedarwood oil, (1 S,2R,5 S,7R,8R)-2,6,6,8-tetramethyltricyclo[5.3.1.01,5]undecan-8-ol (Cedrol), 3-Methyl-5-(2,2,3-trimethyl-3-cyclopenten-1-yl)-4-penten-2-ol (EBANOL®), (R,E)-2-Methyl-4-(2,2,3-trimethylcyclopent-3-enyl) but-2-en-1-ol (HINDINOL®), hinokitiol, DH-ionone beta, [(1R,2S)-1-methyl-2-[[(1R,3 S,5S)-1,2,2-trimethyl-3-bicyclo[3.1.0]hexanyl]methyl]cyclopropyl]methanol (JAVANOL®), 5-butan-2-yl-2-(2,4-dimethyl-1-cyclohex-3-enyl)-5-methyl-1,3-dioxane (karanal), 2,4-Dimethyl-2-(1,1,4,4-tetramethyltetralin-6-yl)-1,3-dioxolane (OKOUMAL®), 1-(1,2,3,4,5,6,7,8-octahydro-2,3,8,8-tatramethyl-2-naphthyl)ethan-1-one (ORBITONE®), 2-ethyl-4-[(1R)-2,2,3-trimethyl-3-cyclopenten-1-yl]-(2E)-buten-1-ol (LEVOSANDOL®), patchouly oil, polysantol, rhubofix, sandalwood, and combinations thereof.

The amounts of the additional fragrance compounds can vary depending on the intended resulting fragrance composition. In certain embodiments, the amounts of additional fragrance compounds can be from about 0.1 parts per thousand to about 999 parts per thousand, or from about 0.1 parts per thousand to about 990 parts per thousand, or from about 0.1 parts per thousand to about 900 parts per thousand, or from about 0.1 parts per thousand to about 800 parts per thousand, or from about 1 part per thousand to about 500 parts per thousand. In particular embodiments, the fragrance composition can include about 0.1 parts per thousand, about 1 parts per thousand, about 10 parts per thousand, about 100 parts per thousand, about 500 parts per thousand, about 800 parts per thousand, about 900 parts per thousand, or about 999 parts per thousand of additional fragrance compounds, based on the total weight of the fragrance composition. Expressed differently, in certain embodiments, the amounts of the additional fragrance compounds can be from about 0.01% to about 99.9%, or from about 0.01% to about 99%, or from about 0.01% to about 90%, or from about 0.01% to about 80%, of from about 0.1% to about 50% by weight, based on the total weight of the fragrance composition. In particular embodiments, the fragrance composition can include about 0.01%, about 0.1%, about 1%, about 10%, about 50%, about 80%, about 90%, or about 99% by weight of additional fragrance compounds, based on the total weight of the fragrance composition.

Such compositions can include at least one ingredient selected from a group consisting of a fragrance carrier and a fragrance base. Such compositions can also further include at least one fragrance adjuvant.

Fragrance carriers can be a liquid or a solid and typically do not significantly alter the olfactory properties of the fragrance ingredients. Some non-limiting examples of fragrance carriers include an emulsifying system, encapsulating materials, natural or modified starches, polymers, gums, pectins, gelatinous or porous cellular materials, waxes, and solvents which are typically employed in fragrance applications.

Fragrance base refers to any composition comprising at least one fragrance co-ingredient. In general, these co-ingredients belong to chemical classes such as, but not limited to: alcohols, aldehydes, ketones, esters, ethers, acetals, oximes, acetates, nitriles, terpenes, saturated and unsaturated hydrocarbons, and essential oils of natural or synthetic origins.

The fragrance compositions according to the disclosed subject matter can be in the form of a simple mixture of the various co-ingredients and solvents, or also in the form of a biphasic system such as an emulsion or microemulsion. Such systems are well-known to persons skilled in the art.

Non-limiting examples of such solvents used in perfumery are known in the art and include but are not limited to: dipropyleneglycol (DPG), diethyl phthalate, isopropyl myristate, benzyl benzoate, 2-(2ethoxy)-1-ethanol, ethyl citrate, triethyl citrate (TEC), ethanol, water/ethanol mixtures, limonene or other terpenes, isoparaffins such as those known under the trademark Isopar® (ExxonMobil Chemicals, Houston, Tex.), and glycol ethers and glycol ether esters such as those known under the trademark Dowanol® (Dow Chemical Company, Midland, Mich.). In particular embodiments, the solvents can include dipropyleneglycol (DPG). In alternate embodiments, the solvents can include dipropyleneglycol (DPG) and triethyl citrate (TEC).

4. Use of Fragrance Compositions in Consumer Products

In certain embodiments, the fragrance compositions of the present disclosure can be formulated as part of a consumer product. Such consumer products can be prepared in any suitable form by any process chosen by the formulator. Suitable consumer products that can include a compound(s) of the presently disclosed subject matter include, but are not limited to, air care products (e.g., candles, aerosols, air fresheners, room sprays and mists, liquid electric air fresheners, fragrance diffusers, gel air fresheners, plug-in air fresheners and oils, wax melts, etc.); baby care products (e.g., consumer products relating to disposable absorbent and/or non-absorbent articles, including adult incontinence garments, bibs, diapers, training pants, infant and toddler care wipes; and personal care products including hand soaps, shampoos, lotions, shower gels, and clothing); fabric and home care products (e.g., consumer products for fabric conditioning (including softening), laundry detergency, laundry and rinse additive and/or care, bleach, dryer sheets, perfume beads, dishwashing, hard surface cleaning and/or treatment, and other cleaning for consumer and or institutional use, etc.); personal care products (e.g., lotions, creams, moisturizers, body washes, hand soaps, shampoos, conditioners, soaps, etc.); family care products (e.g., wet or dry bath tissue, facial tissue, disposable handkerchiefs, disposable towels, and/or wipes, towels, toilet paper, tissue paper, wet towels, etc.); feminine care products (e.g., catamenial pads, incontinence pads, interlabial pads, panty liners, pessaries, sanitary napkins, tampons and tampon applicators, and/or wipes, etc.); sexual health care products (e.g., products relating to sexual aids or sexual health, including lubricants and condoms, etc.); pet care products (e.g., pet malodor cat litter, pet deodorizers, pet health and nutrition including pet foods, treats, other orally deliverable products, grooming aids, products for treating pet hair/fur including shampooing, styling, conditioning; deodorants and antiperspirants; products for cleansing or treating pet skin, including soaps, creams, lotions, and other topically applied products; training aids, toys and diagnostics techniques); fine fragrance (including hydro alcoholic solutions of perfume oil, such as parfum, extrait de parfum, eau de parfum, parfum de toilette, eau de toilette, eau de cologne, body splash, after shave, body mists, including baby colognes); auto care products (e.g., cleaners, air fresheners, wipes, soaps, etc.); cosmetics (e.g., skin cream, cleansing cream, night cream, hand cream, lotion, after-shave lotion, body lotion, foundation, lip stick, lip cream, nail polish, nail polish remover, talcum powder, anti-wrinkle and/or anti-aging cosmetics, sun protection products, massage oil, etc.); beauty care (e.g., products for treating human hair including shampooing, styling, conditioning; deodorants and antiperspirants; products for personal cleansing; products for treating human skin, including application of creams, lotions, and other topically applied products; products for shaving, rinse, rinse in shampoo; hair styling agents such as pomade, hair tonic, hair gel, hair cream and hair mousse; hair growing agents; hair coloring agents, etc.); bath agents (e.g., powder bath additives, solid foaming bath additives, bath oils, bubble bath aroma generators, bath salts, etc.); hair removal products (e.g., products for hair removal including depilatory creams, sugar pastes or gels, waxes); and topical pharmaceuticals (e.g., ointments, creams, and the like used in the treatment and/or prevention of diseases and/or alleviation of symptoms in humans and/or animals). Depending on the solvents that can be present in some end products, it can be necessary to protect the compounds from premature degradation, for example by encapsulation or with a stabilizer, or other methods well-known to those of ordinary skill in the art. In certain embodiments of the present disclosure, the fragrance composition can be admixed with a consumer product wherein the composition is present in an amount from about 0.0001% to about 90% by weight, or from about 0.001% to about 75% by weight, or from about 1% to about 50% by weight, or from about 5% to about 25% by weight, or from about 10% to about 15% by weight, and values in between, based on the total weight of the consumer product. In other embodiments, the fragrance composition can be admixed with a consumer product wherein the composition is present in an amount from about 0.0001% to about 10% by weight, or from about 0.001% to about 5% by weight, or from about 0.001% to about 1% by weight, based on the total weight of the consumer product.

In other embodiments, the consumer product can be such that it comprises from about 90% to about 100% by weight, or from about 95% to about 100% by weight, or from about 99% to about 100% by weight of the fragrance composition, based on the total weight of the consumer product. In particular embodiments, the consumer product can be such that it comprises about 90%, about 95%, about 99%, or about 100% by weight of the fragrance composition, based on the total weight of the consumer product.

In certain embodiments, the consumer product can additionally include one or more bases, solvents, and combinations thereof. A base, as used herein, includes a composition for use in a consumer product to fulfill the specific purpose of the consumer product, such as cleaning, softening, caring, or the like.

In still other embodiments, consumer product bases and/or solvents can include, but are not limited to, essential oils, lactones, aldehydes, alcohols, ketones, nitriles, esters, terpenes, ethers, acetates, acetals, amides, oximes, and additional fragrance ingredients or fragrances.

In some embodiments, the presently disclosed compound(s) can be employed in a consumer product base simply by directly mixing at least one of the presently disclosed compound(s), or a fragrance composition comprising at least one of the presently disclosed compound(s), with the consumer product base, or the presently disclosed compound(s) can, in an earlier step, be entrapped with an entrapment material, for example, polymers, capsules, microcapsules and nanocapsules, liposomes, film formers, absorbents such as carbon or zeolites, cyclic oligosaccharides and mixtures thereof, or it can be chemically bonded to substrates, which are adapted to release the fragrance molecule upon application of an external stimulus such as light, enzymes, or the like, and then mixed with the consumer product base.

In certain embodiments, the fragrance compounds of the present disclosure can be admixed with a consumer product wherein the disclosed fragrance compounds are present in an amount from about 0.00001% to about 20% by weight, or from about 0.0001% to about 10% by weight, or from about 0.001% to about 5% by weight, and values in between, based on the total weight of the consumer product. In particular embodiments, the fragrance compounds of the present disclosure can be admixed with a consumer product wherein the disclosed fragrance compounds are present in an amount of at least about 0.00001% by weight, at least about 0.001% by weight, at least about 5% by weight, or at least about 10% by weight, based on the total weight of the consumer product.

EXAMPLES

The present application is further described by means of the examples, presented below, wherein the abbreviations have the usual meaning in the art.

The use of such examples is illustrative only and does not limit the scope and meaning of the disclosed subject matter or of any exemplified term. Likewise, the disclosed subject matter is not limited to any particular preferred embodiments described herein. Indeed, many modifications and variations of the disclosed subject matter are apparent to those skilled in the art upon reading this specification. The disclosed subject matter is therefore to be limited only by the terms of the appended claims along with the full scope of equivalents to which the claims are entitled.

The following Examples are provided as specific embodiments of the present disclosure, wherein the abbreviations have the usual meaning in the art. The temperatures are indicated in degrees centigrade (° C.); the NMR spectral data were recorded in $CDCl_3$ with a 400 MHz machine for $^1H$ and $^{13}C$, and the chemical displacements are indicated in ppm with respect to TMS as the standard.

Example 1: Synthesis of Compound of Formula I

The compound of Formula I was synthesized as follows:
Wittig salt cis-3-hexenyltriphenlyphosphonium bromide (62.4 g, 1.1 eq.) was added to a flask equipped with an addition funnel. The flask was then purged and flushed with $N_2$. Anhydrous diethyl ether (360 mL) was added to the salt and a slurry was formed. N-BuLi (2.5M in hexanes, 58.8 ml, 1.1 eq.) was added dropwise at room temperature. The reaction mixture was stirred for 1 hour after complete addition to form the ylide. The reaction mixture was then cooled in a bath of acetone and dry ice slurry at about −35° C. Thiophene carboxaldehyde (15 g, 1 eq.) in 135 mL of anhydrous diethyl ether was added dropwise to the cooled reaction mixture. After addition, the reaction was allowed to warm to room temperature gradually and stirred at room temperature overnight. After this time, the reaction mixture was quenched with sat. $NH_4Cl$, extracted with diethyl ether, washed with brine, dried over $MgSO_4$, and filtered. The filtrate was then concentrated. Diethyl ether was added to the crude product to precipitate most of the triphenyl phosphine oxides that were formed. The suspension was filtered, and the filtrate was concentrated under vacuum. Kugelrohr distillation was then employed to separate the products (as a 50/50 mixture of cis-cis and trans-cis isomers) from the remaining triphenyl phosphine oxides (14.0 g, 57% yield). Odor: green, tomato, violet leaf, geranium. GC/MS(EI): m/z (%) 178(28), 163(6), 149(51), 135(52), 123(15), 110(100), 97(69), 79(39), 65(22), 45 (56). $^1H$ NMR ($CDCl_3$): δ0.09 (t, 3H), 2.08 (m, 2H), 2.89/3.13 (t, 2H), 5.51 (vinyl m, 3H), 6.05/6.48 (vinyl m, 1H), 6.97 (m, 2H), 7.25 (m, 1H).

Example 2: Fragrance Composition for Use in a Shampoo

A berry fragrance composition was prepared from the presently disclosed compound to demonstrate use in a shampoo. In this example, the presently disclosed compound was a 50/50 mixture of cis-cis and cis-trans isomers of the compound of Formula I. The presently disclosed compound was a 10% dilution in TEC which was then further diluted to a 10% dilution in DPG. The fragrance composition including the presently disclosed compound is provided in Table 1.

TABLE 1

| FRAGRANCE CATEGORY | PARTS PER THOUSAND | Wt.- % |
|---|---|---|
| Presently Disclosed Compound (@10% in TEC @10% in DPG) | 100 | 10 |
| Animalic | 10 | 1 |
| Floral | 383 | 38.3 |
| Fruity | 261 | 26.1 |

TABLE 1-continued

| FRAGRANCE CATEGORY | PARTS PER THOUSAND | Wt.-% |
|---|---|---|
| Gourmand | 80 | 8 |
| Green | 6 | 0.6 |
| Herbaceous | 10 | 1 |
| Solvent (DPG) | 150 | 15 |
| TOTAL | 1000 | 100 |

A comparative fragrance composition was prepared wherein the presently disclosed compound was replaced with DPG. The comparative fragrance composition is provided in Table 2.

TABLE 2

| FRAGRANCE CATEGORY | PARTS PER THOUSAND | Wt.-% |
|---|---|---|
| Animalic | 10 | 1 |
| Floral | 383 | 38.3 |
| Fruity | 261 | 26.1 |
| Gourmand | 80 | 8 |
| Green | 6 | 0.6 |
| Herbaceous | 10 | 1 |
| Solvent (DPG) | 250 | 25 |
| TOTAL | 1000 | 100 |

The fragrance composition with and without the presently disclosed compound was dosed at 0.8% in a commercial shampoo base. The shampoo, with and without the compound of Formula I, was evaluated by 5 experts in the field of fragrance evaluation. The composition using the presently disclosed compound gave a boost to the overall fragrance strength and added a more natural freshness, compared to the version without the compound of Formula I.

Example 3: Fragrance Composition for Use in Fabric Softener

A peach fragrance composition was prepared from the presently disclosed compound to demonstrate use in a fabric softener. In this example, the presently disclosed compound was a 50/50 mixture of cis-cis and cis-trans isomers of the compound of Formula I. The presently disclosed compound was a 10% dilution in TEC. The fragrance composition is provided in Table 3.

TABLE 3

| FRAGRANCE CATEGORY | PARTS PER THOUSAND | Wt.-% |
|---|---|---|
| Presently Disclosed Compound (@10% in TEC) | 10.0 | 1 |
| Aldehydic | 1.0 | 0.1 |
| Animalic | 2.0 | 0.2 |
| Citrus | 48.0 | 4.8 |
| Floral | 514.2 | 51.42 |
| Fruity | 291.2 | 29.12 |
| Gourmand | 28.0 | 2.8 |
| Green | 11.0 | 1.1 |
| Musk | 34.6 | 3.46 |
| Woody and/or amber | 60 | 6 |
| TOTAL | 1000 | 100 |

A comparative fragrance composition was prepared wherein the presently disclosed compound was replaced with DPG. The comparative fragrance composition is provided in Table 4.

TABLE 4

| FRAGRANCE CATEGORY | PARTS PER THOUSAND | Wt.-% |
|---|---|---|
| Solvent (DPG) | 10.0 | 1 |
| Aldehydic | 1.0 | 0.1 |
| Animalic | 2.0 | 0.2 |
| Citrus | 48.0 | 4.8 |
| Floral | 514.2 | 51.42 |
| Fruity | 291.2 | 29.12 |
| Gourmand | 28.0 | 2.8 |
| Green | 11.0 | 1.1 |
| Musk | 34.6 | 3.46 |
| Woody and/or amber | 60 | 6 |
| TOTAL | 1000 | 100 |

The fragrance composition with and without the presently disclosed compound was dosed at 1% in a fabric softener base. The fabric softener, with and without the compound of Formula I, was evaluated by 5 experts in the field of fragrance evaluation. The composition using the compound of Formula I, gave an exceptional bloom out of aqueous media, and gave a new green freshness to the fragrance, compared to the version without the compound of Formula I.

Although the presently disclosed subject matter and its advantages have been described in detail, it should be understood that various changes, substitutions and alterations can be made herein without departing from the spirit and scope of the application as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the presently disclosed subject matter, processes, machines, manufacture, compositions of matter, means, methods, or steps, presently existing or later to be developed that perform substantially the same function or achieve substantially the same result as the corresponding embodiments described herein can be utilized according to the presently disclosed subject matter. Accordingly, the appended claims are intended to include within their scope such processes, machines, manufacture, compositions of matter, means, methods, or steps.

In addition to the various embodiments depicted and claimed, the disclosed subject matter is also directed to other embodiments having any other possible combination of the features disclosed and claimed herein. As such, the particular features presented herein can be combined with each other in other manners within the scope of the disclosed subject matter such that the disclosed subject matter includes any suitable combination of the features disclosed herein. Thus, the foregoing description of specific embodiments of the disclosed subject matter has been presented for purposes of illustration and description. It is not intended to be exhaustive or to limit the disclosed subject matter to those embodiments disclosed.

It will be apparent to those skilled in the art that various modifications and variations can be made in the device, method, and system of the disclosed subject matter without departing from the spirit or scope of the disclosed subject matter. Thus, it is intended that the disclosed subject matter include modifications and variations that are within the scope of the appended claims and their equivalents.

For any patents, patent applications, publications, product descriptions, and protocols are cited throughout this application, the disclosures of all of which are incorporated herein by reference in their entireties for all purposes.

The invention claimed is:

1. A compound of Formula I:

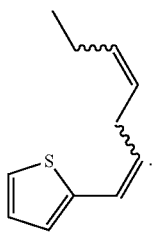

2. A fragrance composition comprising the compound of claim 1.

3. The fragrance composition of claim 2, wherein the composition comprises about a 50/50 mixture of 2-((1Z,4Z)-hepta-1,4-dien-1-yl)thiophene and 2-((1E,4Z)-hepta-1,4-dien-1-yl)thiophene.

4. The fragrance composition of claim 2, wherein the compound of Formula I is present in an amount of from about 0.01% to about 20% by weight, based on the total weight of the fragrance composition.

5. The fragrance composition of claim 2, further comprising one or more compounds selected from the group consisting of one or more aldehydic compound(s), one or more animalic compound(s), one or more balsamic compound(s), one or more citrus compound(s), one or more floral compound(s), one or more fruity compound(s), one or more gourmand compound(s), one or more green compound(s) one or more herbaceous compound(s) one or more marine compound(s), one or more mossy compound(s), one or more musk compound(s), one or more piney compound(s), one or more powdery compound(s), one or more spicy compound(s) and/or one or more woody and/or amber compound(s), and combinations thereof.

6. A consumer product comprising the composition of claim 2.

7. A fragrance composition comprising about a 50/50 mixture of cis-cis isomer and cis-trans isomer of the compound according to claim 1.

8. The fragrance composition of claim 7, wherein the composition comprises about a 50/50 mixture of 2-((1Z,4Z)-hepta-1,4-dien-1-yl)thiophene and 2-((1E,4Z)-hepta-1,4-dien-1-yl)thiophene.

9. The fragrance composition of claim 7, wherein the compound of Formula I is present in an amount of from about 0.01% to about 20% by weight, based on the total weight of the fragrance composition.

10. The fragrance composition of claim 3, further comprising one or more compounds selected from the group consisting of one or more aldehydic compound(s), one or more animalic compound(s), one or more balsamic compound(s), one or more citrus compound(s), one or more floral compound(s), one or more fruity compound(s), one or more gourmand compound(s), one or more green compound(s) one or more herbaceous compound(s) one or more marine compound(s), one or more mossy compound(s), one or more musk compound(s), one or more piney compound(s), one or more powdery compound(s), one or more spicy compound(s) and/or one or more woody and/or amber compound(s), and combinations thereof.

11. A consumer product comprising the composition of claim 7.

12. A consumer product comprising the compound according to claim 1.

* * * * *